(12) United States Patent
Fauconet

(10) Patent No.: US 9,371,261 B2
(45) Date of Patent: Jun. 21, 2016

(54) METHOD FOR PRODUCING BIORESOURCED ACRYLIC ACID FROM GLYCEROL

(75) Inventor: Michel Fauconet, Valmont (FR)

(73) Assignee: ARKEMA FRANCE, Colombes (FR)

( * ) Notice: Subject to any disclaimer, the term of this patent is extended or adjusted under 35 U.S.C. 154(b) by 553 days.

(21) Appl. No.: 13/386,186

(22) PCT Filed: Jun. 29, 2010

(86) PCT No.: PCT/FR2010/051361
§ 371 (c)(1),
(2), (4) Date: Mar. 30, 2012

(87) PCT Pub. No.: WO2011/010035
PCT Pub. Date: Jan. 27, 2011

(65) Prior Publication Data
US 2012/0178965 A1    Jul. 12, 2012

(30) Foreign Application Priority Data

Jul. 22, 2009   (FR) .................................... 09 55111

(51) Int. Cl.
| | | |
|---|---|---|
| *C07C 45/52* | (2006.01) | |
| *C07C 51/235* | (2006.01) | |
| *C07C 51/43* | (2006.01) | |
| *C07C 51/44* | (2006.01) | |
| *C07C 51/48* | (2006.01) | |

(52) U.S. Cl.
CPC ............... *C07C 45/52* (2013.01); *C07C 51/235* (2013.01); *C07C 51/43* (2013.01); *C07C 51/44* (2013.01); *C07C 51/48* (2013.01)

(58) Field of Classification Search
CPC ............... C07C 51/252; C07C 45/38
See application file for complete search history.

(56) References Cited

U.S. PATENT DOCUMENTS

| | | | | |
|---|---|---|---|---|
| 6,482,981 | B2 * | 11/2002 | Ueno et al. ..................... | 562/600 |
| 7,396,962 | B1 * | 7/2008 | Dubois et al. ................. | 568/485 |
| 8,440,859 | B2 * | 5/2013 | Dubois ................... | C07C 45/52 |
| | | | | 562/606 |
| 2001/0020111 | A1 | 9/2001 | Ueno et al. | |
| 2007/0219521 | A1 | 9/2007 | Hird et al. | |
| 2010/0168471 | A1 | 7/2010 | Dubois | |

FOREIGN PATENT DOCUMENTS

| | | | |
|---|---|---|---|
| FR | 2 909 999 A1 | 6/2008 | |
| FR | WO 2010/010298 A2 * | 1/2010 | |

OTHER PUBLICATIONS

White et al, Basic Energy Sciences Advisory Committee Subpanel Workshop Report, Opportunities for Catalysis in the 21st Century, 2002, pp. 1-47.*
Katryniok et al , ACS Catalysis, Recent Developments in the Field of Catalytic Dehydration of Glycerol to Acrolein, 2013, pp. 1819-1834.*
International Search Report of PCT/FR2010/051361 (Nov. 1, 2010).

* cited by examiner

*Primary Examiner* — Paul A Zucker
(74) *Attorney, Agent, or Firm* — Millen, White, Zelano and Branigan, P.C.

(57) ABSTRACT

An aim of the present invention is to produce, from glycerol, a bioresourced acrylic acid, that is to say an acrylic acid essentially based on a carbon source of natural origin, meeting all the quality criteria of monomers customarily used as starting material in processes for polymerization of acrylic acid and of its esters, via an economical process. The process according to the invention comprises a final stage of extraction of acrylic acid by fractional crystallization applied to one of the effluents resulting from the acrylic acid purification chain, the location of this final stage possibly depending on the initial feedstock treated, the nature and the source of the glycerol used in the process, purity specifications to be achieved for the final acrylic acid, or finally economic criteria.

8 Claims, No Drawings

METHOD FOR PRODUCING BIORESOURCED ACRYLIC ACID FROM GLYCEROL

The present invention is targeted at a process for the manufacture of a bioresourced acrylic acid from glycerol as starting material, the term "bioresourced acid" indicating that the acrylic acid is essentially based on a carbon source of natural origin.

Acrylic acid is a very important starting material which can be used directly to produce an acrylic acid polymer or, after esterification with alcohols, to produce a polymer of the corresponding ester. These polymers are used as is or as copolymers in fields as varied as hygiene (for example, in the production of superabsorbants), detergents, paints, varnishes, adhesives, paper, textiles, leather, and the like.

Manufacturers have been developing processes for the synthesis of acrylic acid for decades.

A first generation used, as starting material, compounds comprising a triple bond of acetylenic type which were reacted with a mixture of carbon monoxide and water in the presence of a nickel-based catalyst.

The second generation of processes, which is today the main process for the production of acrylic acid, is based on the oxidation of propylene and/or propane. These starting materials result from oil or natural gas and consequently the acrylic acid is formed from a nonrenewable fossil carbon-based starting material. In addition, the processes for extracting, purifying and synthesizing the starting materials and the processes for destroying, at the end of the cycle, the manufactured finished products based on these fossil starting materials generate carbon dioxide, the latter being a direct byproduct of the reactions for the oxidation of propylene to give acrolein and then of acrolein to give acrylic acid. All this contributes to increasing the concentration of greenhouse gases in the atmosphere. In the context of the commitments of the majority of industrialized countries to reduce emissions of greenhouse gases, it appears particularly important to manufacture novel products based on a renewable starting material, contributing to reducing these environmental effects.

For several years, manufacturers have directed their research and development studies at "bioresourced" synthetic processes using naturally renewable starting materials. Specifically, in order to limit the ecological impact of conventional production processes, alternative processes starting from nonfossil plant starting materials have recently been developed. Examples are processes using, as starting material, 2-hydroxypropionic acid (lactic acid) obtained by fermentation of glucose or molasses originating from the biomass. Further processes are those starting from glycerol (also known as glycerin), resulting from the methanolysis of vegetable oils at the same time as the methyl esters, which are themselves employed in particular as fuels in gas oil and domestic heating oil. This glycerol is a natural product which enjoys a "green" aura; it is available in large amounts and can be stored and transported without difficulty.

The methanolysis of vegetable oils or animal fats can be carried out according to various well-known processes, in particular by using homogeneous catalysis, such as sodium hydroxide or sodium methoxide in solution in methanol, or by using heterogeneous catalysis. Reference may be made on this subject to the paper by D. Ballerini et al. in l'Actuanté Chimique of November-December 2002.

The processes using hydroxypropionic acid as starting material have a major disadvantage from the economic viewpoint. They involve a fermentation reaction which is necessarily carried out under highly dilute conditions in water. In order to obtain acrylic acid, a very large amount of water has to be removed by distillation, at the price of a very high energy cost. Furthermore, the energy expended to separate the water, which energy is produced from fossil material, will be highly damaging to the initial advantage of producing acrylic acid from this bioresourced starting material. Mention may be made, in this field, of application WO2006/092271, which describes a process for the production of polymers from acrylic acid prepared by the enzymatic route, in particular from carbohydrate.

As regards the conversion of glycerol by the chemical route, mention may be made of the two-stage synthesis of acrylic acid, namely the production of acrolein by dehydration of glycerol, which is described in particular in the U.S. Pat. No. 5,387,720, followed by a "conventional" oxidation of the acrolein to produce the acrylic acid. The first stage of the manufacture of acrylic acid from glycerol results in the same intermediate compound as the conventional manufacturing process starting from propylene, namely acrolein, according to the reaction:

which is followed by the second stage of oxidation, according to the reaction:

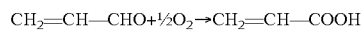

Patent applications EP 1 710 227, WO2006/136336 and WO2006/092272 describe such processes for the synthesis of acrylic acid from glycerol comprising the stage of gas-phase dehydration in the presence of catalysts composed of inorganic oxides (which may or may not be mixed) based on aluminum, titanium, zirconium, vanadium, and the like, and the stage of gas-phase oxidation of the acrolein thus synthesized in the presence of catalysts based on oxides of iron, molybdenum or copper, alone or in combination in the form of mixed oxides.

Acrylic acid is intended for the use by manufacturers of processes for the polymerization either of acrylic acid or of its ester derivatives, which processes are carried out under various forms, in bulk, in solution, in suspension or in emulsion. These processes can be highly sensitive to the presence in the charge of certain impurities, such as aldehydes or unsaturated compounds, which can sometimes prevent the expected use value from being obtained, for example by limiting the conversion of the monomer to give the polymer, by limiting the chain length of the polymer or by interfering in the polymerization in the case of unsaturated compounds. Other impurities, such as nonpolymerizable saturated compounds, can be particularly troublesome in the final application by modifying the properties of the finished product, by conferring toxic or corrosive properties on the finished product or by increasing polluting organic discharges during the stages of manufacture of the polymer and/or of the finished product.

Operators are proving to be demanding as regards quality specifications for acrylic acid (or for its ester). The latter must meet strict thresholds as regards impurities. Specifically, users of acrylic acid or of acrylic esters which produce polymers employ formulations suited to the production of their polymers from a "standard" grade of acrylic acid or of esters today manufactured solely from propylene. A modification to the formulations used by these users, for the purpose of adapting them to a different grade of acrylic acid or of esters produced by a route other than that of the conventional ex-propylene processes, would exhibit significant disadvantages for these user companies. Apart from the additional research and development costs, the production of one type of polymer on the same unit starting from different grades of acrylic acid or of esters according to their origin, fossil or bioresourced (such as glycerol), would occasion significant conversion costs and a more complicated production infrastructure. As the grade of the acrylic acid, that is to say its content of various impurities, plays a major role in the subsequent polymerization processes, the manufacturers manufacturing this acrylic acid have been led to deploy a whole series of purification stages in order to obtain this "standard" acrylic acid which is normally referred to as glacial acrylic acid (GAA). This GAA does not correspond to specifications officially recognized and having a universal nature but means, for each manufacturer, the level of purity to be achieved in order to be able to successfully carry out his subsequent conversions. By way of example, for an ex-propylene acrylic acid, the reactor outlet effluent stream is subjected to a combination of stages which can differ in their sequence according to the process: removal of the noncondensable compounds and most of the very light compounds, in particular the intermediate acrolein for the synthesis of the acrylic acid (crude AA), dehydration removing the water and the formaldehyde (dehydrated AA), removal of the light compounds (in particular acetic acid), removal of the heavy compounds, and optionally removal of some residual impurities by chemical treatment.

The invention is targeted at a process for the manufacture of a "standard" acrylic acid by using glycerol as starting material which will be converted in two stages—dehydration and oxidation—as mentioned above, incorporated in an overall purification process.

This process is highly analogous to the synthesis process starting from propylene insofar as the intermediate product, acrolein, resulting from the first stage is the same and in that the second stage is carried out under the same operating conditions. However, the reaction of the first stage of the process of the invention, the dehydration reaction, is different from the reaction for the oxidation of propylene of the normal process. The dehydration reaction, performed in the gas phase, is carried out using solid catalysts different from those used for the oxidation of propylene. The acrolein-rich effluent stream resulting from the first dehydration stage, intended to feed the second stage of oxidation of the acrolein to give acrylic acid, comprises a greater amount of water and additionally exhibits substantial differences as regards byproducts resulting from the reaction mechanisms involved being given material form by different selectivities in each of the two routes.

In order to illustrate these differences, the data relating to the presence of various acids in the crude acrylic acid, that is to say in the liquid phase exiting from the second-stage reactor, are collated in the following table 1.

TABLE 1

| Impurity/AA ratio by weight (crude acrylic acid) | Ex-propylene process | Ex-glycerol process |
|---|---|---|
| Acetic acid/AA | <5% | >10% |
| Propionic acid/AA | <0.1% | >0.5% |
| 2-Butenoic acid/AA | <0.001% | >0.01% |

The impurities/AA ratios depend on the catalysts used, on their "age" (deterioration in the selectivities over time) and on the operating conditions. In table 1, the 2-butenoic acid/AA ratio is given as <0.001% for the ex-propylene process; however, although the Applicant Company has never detected it in ex-propylene AA, it considers it preferable to write "<10 ppm" rather than 0% (result of its analysis) in order to eliminate the problem of detection threshold related to the analytical method.

Some of the main differences, in terms of constituents of the liquid effluent stream exiting from the oxidation reactor, between the ex-propylene and ex-glycerol processes are illustrated in table 1. Naturally, although this is not mentioned in the table, there is also found, in the crude acrylic acid, whether it originates from the ex-propylene process or from the ex-glycerol process, a whole series of oxygen-comprising compounds, alcohols, aldehydes, ketones, other acids, and the like, the necessary separation of which is known to a person skilled in the art.

The specifications for the acrylic acid grades commonly used for the production of acrylic acid and acrylic ester polymers require reducing the contents of the impurities of table 1 in acrylic acid down to the values which appear in table 2 below.

TABLE 2

| Concentration of the impurities in the AA (by weight) | Technical acrylic acid for esterification | Glacial acrylic acid for polymerization |
|---|---|---|
| Acetic acid | <0.2% | <0.1% |
| Propionic acid | <0.05% | <0.05% |
| 2-Butenoic acid | <0.005% | <0.001% |

The acetic acid and the propionic acid are troublesome in particular because they are not converted during the polymerization process; they are saturated and thus cannot be polymerized. According to the polymerization process involved and the applications targeted for the polymer, these impurities may remain in the finished product and risk conferring undesirable corrosive properties on the finished product or may be found in the liquid or gaseous discharges generated by the polymerization process and cause equally undesirable organic pollution.

The 2-butenoic acid, not synthesized by the ex-propylene process but present in both its configurations (E, also known as crotonic acid, CAS No.: 107-93-7, and Z, also known as isocrotonic acid, CAS No.: 503-64-0) in the ex-glycerol process, is for its part particularly troublesome because, due to its double bond, it is capable of participating in the polymerization process and thus of modifying the characteristics and the use value of the final polymer.

In order to achieve the acrylic acid grades cited in table 2, the removal of the acetic acid may be obtained by distillation in a light fraction, operation generally denoted by the term topping. However, the reduction of the concentration of acetic acid within the context of the ex-glycerol process leads to a consequent loss of acrylic acid in the light fraction, due, on the one hand, to the large difference that exists between its initial content in the crude acrylic acid and its targeted content in the technical acrylic acid for esterification and, on the other hand, to the existence of hydrogen bonds that exist between the carboxylic groups of the two molecules. This drawback is significant from an economic viewpoint, since obtaining a glacial acrylic acid having an acetic acid content of less than 0.1% by weight can only be achieved to the detriment of the recovery ratio of acrylic acid exiting the oxidation reactor.

The reduction of the content of 2-butenoic acid via a distillation route must be obtained by passing into a heavy fraction, the latter separation proving, however, difficult.

As regards the propionic acid, the extremely small difference in volatility that exists between this impurity to be removed and the acrylic acid to be purified (of the order of 1° C.) prevents any purification under economically acceptable conditions via distillation.

The objective of the present invention is to produce, from glycerol, an acrylic acid meeting all the quality criteria of monomers customarily used as starting material in processes for the polymerization of acrylic acid and esters, via an economical process.

A subject matter of the invention is a process for the manufacture of bioresourced acrylic acid from glycerol, comprising the following stages:
- gas-phase catalytic dehydration of glycerol to give acrolein, (1)
- partial condensation by cooling and extraction of a portion of the water present in the reaction medium of (1), (1')
- gas-phase catalytic oxidation of the acrolein to give acrylic acid, (2)
- extraction of the acrylic acid present in the effluent stream from the oxidation by water absorption with cooling and removal of the light fraction that is rich in noncondensable very light gaseous compounds, (3)
- drying of the acrylic acid solution by distillation in the presence of a solvent that is immiscible with water, (4)
- distillation of the solution thus obtained in order to remove the light compounds (topping), (5)
- distillation of the heavy fraction resulting from the preceding stage (5) in order to remove the heavy compounds (tailing), (6)

combined with a final stage of extraction of the acrylic acid by fractional crystallization applied to one of the following effluent streams: the heavy fraction from (4), the heavy fraction from (5) or the light fraction from (6).

Use is generally made, for the implementation of the process, of a stream feeding the reactor of stage (1) comprising glycerol and water with a water/glycerol ratio by weight which can vary within wide limits, for example between 0.04/1 and 9/1 and preferably between 0.7/1 and 3/1. The dehydration reaction, stage (1), which is an equilibrium reaction but one promoted by a high temperature level, is generally carried out in the gas phase in the reactor in the presence of a catalyst at a temperature ranging from 150° C. to 500° C., preferably between 250° C. and 350° C., and an absolute pressure between 1 and 5 bar (100 and 500 kPa). It can also be carried out in the presence of oxygen or of an oxygen-comprising gas, as described in applications WO 06/087083 and WO 06/114506.

The glycerol dehydration reaction is generally carried out over solid acid catalysts. The catalysts which are suitable are substances used in a gaseous or liquid reaction medium, in the heterogeneous phase, which have a Hammett acidity, denoted $H_0$, of less than +2. As indicated in U.S. Pat. No. 5,387,720, which refers to the paper by K. Tanabe et al. in "Studies in Surface Science and Catalysis", Vol. 51, 1989, chap. 1 and 2, the Hammett acidity is determined by amine titration using indicators or by adsorption of a base in the gas phase.

These catalysts can be chosen from natural or synthetic siliceous substances or acidic zeolites; inorganic supports, such as oxides, covered with mono-, di-, tri- or polyacidic inorganic acids; oxides or mixed oxides or heteropolyacids or heteropolyacid salts.

These catalysts can generally be composed of a heteropolyacid salt in which the protons of said heteropolyacid are exchanged with at least one cation chosen from elements belonging to Groups I to XVI of the Periodic Table of the Elements, these heteropolyacid salts comprising at least one element chosen from the group consisting of W, Mo and V.

Mention may particularly be made, among mixed oxides, of those based on iron and on phosphorus and of those based on cesium, phosphorus and tungsten.

The catalysts are chosen in particular from zeolites, Nafion® composites (based on sulfonic acid of fluoropolymers), chlorinated aluminas, phosphotungstic and/or silicotungstic acids and acid salts, and various solids of the type comprising metal oxides, such as tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silicoaluminate $SiO_2/Al_2O_3$, impregnated with acid functional groups, such as borate $BO_3$, sulfate $SO_4$, tungstate $WO_3$, phosphate $PO_4$, silicate $SiO_2$ or molybdate $MoO_3$ functional groups, or a mixture of these compounds.

The preceding catalysts can additionally comprise a promoter, such as Au, Ag, Cu, Pt, Rh, Pd, Ru, Sm, Ce, Yt, Sc, La, Zn, Mg, Fe, Co, Ni or montmorillonite.

The preferred catalysts are phosphated zirconias, tungstated zirconias, silica zirconias, titanium or tin oxides impregnated with tungstate or phosphotungstate, phosphated aluminas or silicas, heteropolyacids or heteropolyacid salts, iron phosphates and iron phosphates comprising a promoter.

The reaction medium exiting from the dehydration reactor has a high water content due to the glycerol charge (aqueous solution) and the reaction itself. An additional stage (1') of partial condensation of the water, such as, for example, that described in patent application WO 08/087315 on behalf of the Applicant, will make it possible to remove a portion thereof, so as to bring this gas to a composition substantially identical to that of the ex-propylene process, in order to feed the second stage of oxidation of the acrolein to give acrylic acid. The term "composition substantially identical" is understood to mean in particular similar acrolein, water and oxygen concentrations. This condensation stage (1') has to be carried out with cooling to a temperature which makes it possible to obtain, after removal of the condensed phase, a gas stream comprising water and acrolein in a water/acrolein molar ratio of 1.5/1 to 7/1. This partial condensation of the water makes it possible to prevent damage to the catalyst of the $2^{nd}$ stage of oxidation of the acrolein to give acrylic acid and to prevent, during the subsequent stages, the removal of large amounts of water, which is expensive and which presents the risk of resulting in losses of acrylic acid. In addition, it makes it possible to remove a portion of the "heavy" impurities formed during the dehydration.

The oxidation reaction, stage (2), is carried out in the presence of molecular oxygen or of a mixture comprising molecular oxygen, at a temperature ranging from 200° C. to 350° C., preferably from 250° C. to 320° C., and under a pressure ranging from 1 to 5 bar, in the presence of an oxidation catalyst.

Use is made, as oxidation catalyst, of any type of catalyst well-known to a person skilled in the art for this reaction. Use is generally made of solids comprising at least one element chosen from the list Mo, V, W, Re, Cr, Mn, Fe, Co, Ni, Cu, Zn, Sn, Te, Sb, Bi, Pt, Pd, Ru and Rh, present in the metallic form or in the oxide, sulfate or phosphate form. Use is made in particular of the formulations comprising Mo and/or V and/or W and/or Cu and/or Sb and/or Fe as main constituents.

The gas mixture resulting from stage (2) is composed, apart from acrylic acid:
- of light compounds which are noncondensable under the temperature and pressure conditions normally employed: nitrogen, unconverted oxygen, carbon monoxide and carbon dioxide, which are formed in a small amount by final oxidation, of condensable light compounds: in particular water, generated by the dehydration reaction or present as diluent, unconverted acrolein, light aldehydes, such as formaldehyde and acetaldehyde, formic acid, acetic acid and propionic acid, of heavy compounds: furfuraldehyde, benzaldehyde, maleic acid, maleic anhydride, 2-butenoic acid, benzoic acid, phenol and protoanemonin.

Stage (3) consists of an extraction of the acrylic acid by a countercurrent absorption with water. For this, the gas resulting from the reactor is introduced at the bottom of an absorption column where it meets, countercurrently, water introduced at the top of the column. The light compounds (mainly acetaldehyde and acrolein) are for the most part removed at the top of this absorption column. The water used as absorbent solvent may be introduced via a source external to the process, but will preferably be constituted, partly or completely, by recovery from at least one of the reaction gas streams resulting from the initial reaction stages, for example the water resulting from stages (1') and (4), namely the water condensed in stage 1', or the water recovered from the top stream of the azeotropic drying column. The operating conditions of this absorption stage are the following:

The gaseous reaction mixture is introduced at the bottom of the column at a temperature between 130° C. and 250° C. The water is introduced at the top of the column at a temperature between 10° C. and 60° C. The respective amounts of water and of gaseous reaction mixture are such that the water/acrylic acid weight ratio is between 1/1 and 1/4. The operation is carried out at atmospheric pressure.

In one preferred implementation variant of the process, during a stage (3') the acrolein, contained in the liquid fraction resulting from (3), is recovered by distillation or stripping with a gas. In this variant of the process, the absorption column may be coupled to a column for distillation of very light compounds, essentially acrolein unconverted at the end of the reaction, present at low concentration in the aqueous acrylic acid solution recovered at the bottom of the absorption column. This distillation column, operating under a pressure of $6 \times 10^3$ to $7 \times 10^4$ Pa, is fed at the top by the stream from the bottom of the preceding absorption column, and makes it possible to remove, at the top, a stream of acrolein-enriched acrylic acid, which is recycled to the lower part of the absorption column (3), for a final removal at the top of this same column. Thus, an aqueous mixture of acrylic acid in water (1/1 to 4/1 weight ratio) stripped of most of the unconverted acrolein is obtained, which is referred to as "crude acrylic acid". The recovery of the acrolein may also be carried out by stripping with a gas such as air or a mixture of inert gases preferably containing oxygen.

This stage is optional but in its absence the crude acrylic acid will be more concentrated in acrolein which will have to be removed during the subsequent topping stage. Furthermore, this stage (3') makes it possible to recover and recycle the acrolein to the reaction section (2) and thus to increase the overall yield of the process.

Stage (4) is a dehydration or drying stage which is carried out in the presence of a solvent of acrylic acid that is immiscible with water. This dehydration stage may be carried out by liquid-liquid extraction of the acrylic acid in the presence of the solvent, followed by a stage of separation of the monomer, acrylic acid, by distillation.

This dehydration phase is described in many patents, see for example patent FR 2 119 764, with methyl isobutyl ketone (MIBK) as solvent, or U.S. Pat. No. 3,689,541, with trimethylcyclohexanone as solvent, or by distillation in the presence of solvent or mixtures of solvents forming a heterogeneous azeotrope with water, such as acetates or methyl isobutyl ketone, as described for example in patent FR 2 554 809 or else solvents that form, in addition, an azeotropic mixture with acetic acid such as toluene, as described for example in patent JP 03 181 440.

In the process of the invention, use will preferably be made, for this dehydration stage, of an azeotropic distillation using a solvent such as MIBK. The distillation column, which operates under a pressure of $6 \times 10^3$ to $7 \times 10^4$ Pa, is equipped with a decanter that receives the stream from the top of the column after condensation and ensures the separation of an upper organic phase essentially constituted of MIBK, completely recycled under reflux to the top of the column, and of an aqueous phase containing water and most of the formaldehyde. The heating power imposed on the reboiler of the column is regulated so as to obtain a solvent reflux flow rate such that the weight ratio of solvent sent back under reflux and of water contained in the crude acrylic acid feeding the column corresponds to the theoretical azeotropic mixture. The stream obtained at the bottom of the column, the dehydrated acrylic acid, is essentially free of water (generally less than 1% by weight).

In one embodiment variant, this column may be coupled to a second column for recovery of the solvent, so as to recover in the aqueous stream decanted at the top of the azeotropic distillation column, traces of solvent dissolved in the aqueous phase. These small amounts of solvent which are distilled and condensed at the top of this solvent recovery column, operating under atmospheric pressure, are then recycled into the decanter of the preceding column. The aqueous stream from the bottom of this solvent recovery column is removed.

Stage (5) is a stage of removing light compounds, in particular acetic acid and formic acid, by distillation; it is generally known as "topping". The dehydrated acrylic acid stream obtained at the bottom of the azeotropic distillation column is sent to the middle part of a distilling column which operates under an overhead pressure of the order of $2 \times 10^3$ to $2 \times 10^4$ Pa. The stream from the bottom of the column contains acrylic acid stripped of most of the light compounds. The stream from the top of the column, rich in acetic acid and formic acid, may optionally be additionally treated in order to recover, in a second column in series, the small amounts of acrylic acid entrained with the stream from the top of the column.

Stage (6) is a stage of separation of the heavy compounds by distillation. The stream from the bottom of the preceding topping column is introduced into the bottom of a distillation column operating under an overhead pressure of the order of $2 \times 10^3$ to $2 \times 10^4$ Pa. At the top a stream of purified acrylic acid, referred to as technical grade, is obtained.

The various stages of separation by distillation require, due to the thermodynamic conditions employed, the addition to the treated streams of polymerization inhibitors in order to prevent the formation of heavy compounds formed by polymerization of acrylic acid, which are prejudicial to the satisfactory operation of the assembly. The polymerization inhibitors generally used for the stages for the purification of the acrylic acid are phenolic products, such as hydroquinone or hydroquinone methyl ether, phenothiazine derivatives, compounds of the family of the thiocarbamates, such as copper di(n-butyl)dithiocarbamate, amino derivatives, such as hydroxylamines, hydroxydiphenylamine or derivatives of the family of the phenylenediamines, nitroxide derivatives of 4-hydroxy-2,2,6,6-tetramethylpiperidin-1-oxyl (TEMPO), such as 4-hydroxy-TEMPO or 4-oxo-TEMPO, or metal salts, such as manganese acetate. These inhibitors can be used alone or in combination and are in addition preferably introduced in combination with an oxygen-comprising gas.

These polymerization inhibitors are generally heavy compounds, the volatility of which is lower than that of acrylic acid. They are removed at the bottom of the columns. On the other hand, their concentration in the vapor phase inside the distillation columns is low and insufficient to prevent the initiation of polymers. In order to prevent the appearance and the accumulation of polymers, these additives are usually introduced into the liquid streams feeding the devices, but also at the top and at various points of the columns and devices, so as to provide continuous and homogeneous reflux of solution rich in polymerization inhibitors over all the parts of the devices. Generally, they are conveyed in solution in a liquid, for example in acrylic acid or in water, if the purification stage relates to aqueous streams.

In the process of the invention, the final stage of the procedure for the purification of the bioresourced acrylic acid is a separation by fractional crystallization thus combined with the preceding purification stages.

Fractional crystallization is a well-known separation technique. It can be carried out in various forms, dynamic crystallization, static crystallization or suspension crystallization. Mention may be made, on this subject, of French patent 77 04510 of 17/02/1977 (BASF) and U.S. Pat. No. 5,504,247 (Sulzer) and U.S. Pat. No. 5,831,124 (BASF) and U.S. Pat. No. 6,482,981 (Nippon Shokubai), some of which are targeted at the purification of acrylic acid synthesized by the oxidation of propylene.

The most widely used technique is falling film fractional crystallization, dynamic crystallization, optionally combined with molten medium static crystallization.

Falling film crystallization is generally carried out in a tubular exchanger, in practice multitubular, each tube being fed continuously (at the top) with:

a liquid stream (solution or melt) of the compound to be purified, acrylic acid (AA) in the process, falling as a film, preferably along the internal wall of the tube, received at the tube bottom and recycled at the top (closed loop) for the time necessary for the crystallization of the amount of compound (AA) decided upon by the operator, a stream of heat-exchange fluid, for example ethylene glycol/water or methanol/water, falling as a film, preferably along the external wall of the tube, also recirculated throughout the crystallization within the tube and which will introduce the cold or the heat necessary for the operation of the stages of each of the steps.

The process is a combination of successive steps, which each comprise 3 stages:

crystallization: the temperature of the heat-exchange fluid is lowered according to a negative temperature gradient from a temperature slightly greater than the crystallization temperature of the acrylic acid in the medium, of the order of 14° C. Crystals are formed as an increasingly thick layer at the surface of the tubes. When approximately from 30 to 80% of AA circulated has crystallized, after draining, the remaining liquid fraction (mother liquors rich in impurities) is transferred into a receiver.

sweating: the temperature of the heat-exchange fluid is increased according to a positive temperature gradient in order to remove, by melting, the impurities trapped in the form of inclusions in the layer of acrylic acid crystals being formed; these are mainly located in the outermost layer which is in contact with the recirculated stream increasingly rich in impurities. During the sweating, the first molecules to melt are eutectic mixtures of impurities and of AA, the impurities located in the layer of crystals migrate towards the outer layer, i.e. that which was in contact with the recirculated stream. A small portion of this layer of crystals is thus melted and transferred into a receiver, preferably the same receiver as that for the mother liquors recovered during the crystallization stage. This sweating stage can be replaced by a washing technique, which consists in removing the impurities present at the surface by washing with pure AA, preferably introduced at a temperature slightly greater than the melting point of the layer of AA. However, this technique is a priori less effective.

melting: the temperature of the heat-exchange fluid is rapidly increased above the melting point of AA (14° C.) and should preferably remain below a maximum temperature above which polymerization (explosive) of the medium may be feared: this maximum temperature is of the order of 35-40° C. in order to remain safe in melting the layer of crystals of purified AA. The purified liquid recovered is placed in a second receiver.

Starting from the stream to be purified, the combination of the three stages described represents a first purification step. The purified liquid resulting from this first step can again be subjected to a sequence of the three stages described in a $2^{nd}$ purification step (purification phase). The mother liquors resulting from this $2^{nd}$ step are purer than those from the preceding step and can thus be used as a mixture with a new charge of AA to be purified in step No. 1. The same operation can be carried out in a third purification step, it being possible for the mother liquors from this third step to be recycled in the charge of the $2^{nd}$ step, the pure product being recovered by melting the crystals. Generally, the mother liquors from the "n" purification step can be recycled by mixing them with the feed stream for the "n−1" purification step.

During the purification phases, the polymerization inhibitors present in the mixtures to be purified are treated like impurities and are thus removed in the mother liquors. In order to prevent the formation of polymers in the molten crystallisate, an inhibitor compatible in nature and concentration with the final use of the monomer is preferably added. This addition will in particular be carried out during the final melting stage of a step fed with a stream devoid of polymerization inhibitor, such as, for example, the final "n" purification step fed solely with a purified stream from the "n−1" step.

The mother liquors collected subsequent to the first purification step can be treated in a "−1" step according to the same three-stage process. The crystallisate recovered can be used as supplement for the feed charge of the first step. The mother liquors from the "−1" step are then treated according to the same process for a new separation, the crystallisate of which will participate as charge for the immediately greater step and the mother liquors of which are again subjected to the process in a lower "−2" step. The "−1", "−2", and the like, steps constitute the concentration steps (the successive steps make it possible to concentrate the impurities in the mother liquor streams). Generally, the mother liquors from the "n" concentration steps are treated according to the same three-stage process in the subsequent "n−1" step. The repetition of these operations (concentration phase) will make it possible to concentrate the impurities in a mother liquor stream increasingly rich in impurities, while the pure acrylic acid fractions will be returned to the initial step. Thus, the acrylic acid entrained in the initial mother liquors can be recovered in order to improve the recovery yield and, furthermore, a mixture "enriched" in impurities can be obtained.

The successive concentration steps are characterized by mother liquor streams which are increasingly concentrated in impurities as these steps pile up. In doing this, the crystallization temperature of these mixtures becomes increasingly low, which has the effect of increasing the energy cost of the cooling. Furthermore, the time necessary to crystallize the same amount of acrylic acid becomes increasingly lengthy, which has the consequence of reducing the productive output of the purification for the same crystallization surface area. Consequently, the number of the concentration steps will preferably generally be halted before the total concentration of impurities in the mother liquors exceeds 50% by weight of the stream.

Depending on the purity of the starting material, the purity of the expected purified product and the AA recovery yield desired, the complete process for an initial AA grade of "technical" type generally comprises between 1 and 4 purification steps, and between 1 and 4 steps for the concentration of the impurities.

In order to further improve the recovery yield, it is also possible to carry out the final step of concentration in a static crystallizer. In this case, the mixture to be crystallized is placed in contact with a cold wall. It can, for example, be an exchanger composed of metal sheets, through which a heat-exchange fluid passes, immersed in a vessel comprising the crystallization mother liquors from the preceding steps. The AA forms a crystal layer on the wall of the sheets, the mother liquors are then removed and the crystallized layer is melted in order to be subsequently treated in a higher step of falling film dynamic crystallization.

Among the problems posed by the treatment of the liquid phase of the effluent stream resulting from the oxidation reactor is the presence of a very large amount of acetic acid, the separation of which at the topping stage (stage 5) is tricky as was indicated previously and which involves the use of a column comprising a large number of plates leading to significant pressure and temperature differences between the bottom and the top of the column. In the case of the use of a purification stage via crystallization downstream of this topping stage, the operating conditions of the latter for removing the acetic acid will be able to be simplified by targeting a less drastic degree of removal. Indeed, the residual acetic acid at the end of the topping stage, will be able to be removed during the subsequent crystallization stage. The saving which will be able to be induced by the crystallization stage over the topping stage is therefore a reduction in the number of theoretical stages of the distillation column (therefore in the height of the column) and consequently an investment saving. A second advantage is a reduction in the temperature at the bottom of the column, imposed by the pressure loss in the column, itself proportional to the number of plates, and consequently a reduction in the risk of formation of heavy compounds of the type of acrylic acid dimer (β-acryloxy-propionic acid) and polymers.

The location of the final crystallization stage in the purification chain of the acrylic acid will depend on the initial feedstock treated, the nature and the source of the glycerol used in the process, purity specifications to be achieved for the final acrylic acid and finally economic criteria linked to the cost savings in the distillations compared to a cost premium due to an increase in the number of crystallization stages.

The application of the treatment by fractional crystallization to the light fraction of stage (6) has the advantage of fully achieving the objectives desired in the present application with a recovery yield of acrylic acid that is particularly efficient in the last crystallization stage (greater than 97%) and an overall yield of purification better than that of the conventional process by distillation with a degree of purity of the acrylic acid that is at least as good.

The application of the treatment by fractional crystallization to the heavy fraction of stage (4) makes it possible to reduce the investment costs of the unit by reducing the number of purification columns and also the material costs, such as the polymerization inhibitors. Moreover, the risk of fouling via polymerization is reduced. The recovery yield of the last crystallization stage (>90%) is not as good as in the preceding case, but the overall recovery yield remains better than that of the conventional process via distillation.

The application of the treatment by fractional crystallization to the heavy fraction of stage (5) is intermediate between the first two, with an overall recovery yield which remains greater than that of the conventional process via distillation.

The invention also relates to the use of the bioresourced acrylic acid obtained according to the process of the invention in the manufacture of homopolymers and copolymers produced by polymerization of acrylic acid and optionally of other unsaturated monomers, for example the manufacture of superabsorbent polymers obtained by polymerization of said partially neutralized acid or the polymerization of said acid, followed by a partial neutralization of the polyacrylic acid obtained.

The invention also relates to the polymers and copolymers obtained by polymerization of bioresourced acrylic acid and optionally of other bioresourced monomers or monomers resulting from fossil starting materials.

The invention also relates to the superabsorbants obtained by polymerization of bioresourced acrylic acid.

The invention is also targeted at the use of bioresourced acrylic acid in the manufacture of polymers or copolymers by polymerization of the derivatives of said acid in the ester or amide form. It is also targeted at the polymers or copolymers obtained by polymerization of the derivatives, in the ester or amide form, of bioresourced acrylic acid.

The process for the manufacture of acrylic acid according to the invention is illustrated by the following examples.

EXAMPLE 1

Manufacture of Crude Acrylic Acid from Glycerol

The preliminary stage consists in purifying the crude glycerol obtained from vegetable oil, with removal of the salts. The crude glycerol solution is composed, by weight, of 89.7% of glycerol, 3.9% of water and 5.1% of sodium chloride. This stream (6400 g) is continuously conveyed as feed to a stirred 2-liter reactor heated by an external electrical reactor heater. The glycerol and water vapors are condensed in a reflux condenser and recovered in a receiver. This purification operation is carried out under a pressure of 670 Pa (5 mmHg). 5710 g of a glycerol solution devoid of sodium chloride are obtained. Moving on to stage (1) of the process, the reaction for the dehydration of the glycerol to give acrolein and the condensation (1') of a portion of the water are carried out. The dehydration reaction is carried out in the gas phase in a fixed bed reactor in the presence of a solid catalyst composed of a tungstated zirconia $ZrO_2/WO_3$ at a temperature of 320° C. at atmospheric pressure. A mixture of glycerol (20% by weight) and water (80% by weight) is conveyed to an evaporator in the presence of air in an $O_2$/glycerol molar ratio of 0.6/1. The gas medium exiting from the evaporator at 290° C. is introduced into the reactor, composed of a tube with a diameter of 30 mm charged with 390 ml of catalyst and immersed in a salt bath ($KNO_3$, $NaNO_3$ and $NaNO_2$ eutectic mixture) maintained at a temperature of 320° C.

At the outlet of the reactor, the gaseous reaction mixture is conveyed to the bottom of a condensation column. This column is composed of a lower section filled with Raschig rings surmounted by a condenser in which a cold heat-exchange fluid circulates. The cooling temperature in the exchangers is adjusted so as to obtain, at the column top, a temperature of the vapors of 72° C. at atmospheric pressure. Under these conditions, the loss of acrolein at the condensation column bottom is less than 5%.

In the following stage (2), the gas mixture is introduced, after addition of air ($O_2$/acrolein molar ratio of 0.8/1) and of nitrogen in an amount necessary in order to obtain an acrolein concentration of 6.5 mol %, as feed of the reactor for the oxidation of acrolein to give acrylic acid. This oxidation reactor is composed of a tube with a diameter of 30 mm charged with 480 ml of a commercial catalyst for the oxidation of acrolein to give acrylic acid based on mixed oxides of aluminum, molybdenum, silicon, vanadium and copper and immersed in a salt bath, identical to that described above, maintained at a temperature of 345° C. Before introduction over the catalytic bed, the gas mixture is preheated in a tube which is also immersed in the salt bath.

At the outlet of the oxidation reactor, the gas mixture is introduced at the bottom of an absorption column, stage (3), operating at atmospheric pressure. This column is filled with random stainless steel packing of the ProPak type. In the lower part, over ⅓ of its total height, the column is equipped with a condensation section, at the top of which is recycled a portion of the condensed mixture recovered at the column bottom, after cooling in an external exchanger. The upper part of the column is cooled by heat exchange through the wall. The temperature of the vapors at the top of the column is 25° C., that of the aqueous solution of crude acrylic acid obtained at the bottom of the column is 35° C. The product obtained as bottoms (crude acrylic acid) contains 40% of water and a mixture of acrylic acid (major product) and of impurities, present in the "impurities/AA" weight ratios indicated in table 3 below. Introduced continuously, into the recirculation loop at the bottom of the column, is an aqueous solution of hydroquinone (HQ), at a concentration of 0.1% by weight relative to the acrylic acid.

EXAMPLE 2 (COMPARATIVE)

Manufacture of Crude Acrylic Acid from Propylene

The reactor for oxidation of propylene to acrylic acid is constituted of 2 reaction tubes in series, immersed in independent compartments containing baths of heated molten salts (eutectic mixture of 53% $KNO_3$, 40% $NaNO_2$ and 7% $NaNO_3$). The 2 reaction tubes have a height of 1 m, a diameter of 25 mm and are filled respectively with a commercial catalyst for the oxidation of propylene to acrolein, which catalyst is based on oxides of molybdenum, bismuth, iron and silicon and with a catalyst for the oxidation of acrolein to acrylic acid which is identical to that used in example 1. The salt bath of the compartment containing the first reaction tube is heated at a temperature of 362° C., that of the 2nd reaction stage at a temperature of 345° C. The first reaction tube is fed at a flow rate of 546 Nl/h with a mixture constituted, by volume, of 7% propylene, 7% water, 26% nitrogen and 60% air. The reaction gas exiting the tube is sent into the second reaction tube.

The reaction stream exiting the second reactor is sent to the bottom of an absorption column identical to that from example 1, under the same conditions as this example 1. The product obtained as bottoms (crude acrylic acid) contains 35% water and a mixture of acrylic acid (major product) and of impurities, present in the "impurities/AA" weight ratios indicated in table 3 below.

TABLE 3

| "Impurities/acrylic acid" weight ratios | Example 1 | Example 2 |
|---|---|---|
| Formaldehyde | 0.38% | 1.37% |
| Acetic acid | 14.44% | 3.27% |
| Propionic acid | 0.81% | 0.05% |
| Furfural | 0.01% | 0.02% |
| Protoanemonin | 0.02% | 0.02% |
| Benzaldehyde | 0.03% | 0.03% |
| Trans-2-butenoic (crotonic) acid | 0.04% | 0.00% |
| Maleic acid | 0.41% | 0.67% |

EXAMPLE 3

Purification of the Crude AA Obtained Ex-Glycerol to Technical AA

The aqueous solution obtained is subjected to a drying stage (4) via a distillation in order to remove the water in the form of an azeotropic mixture with methyl isobutyl ketone (MIBK). The column, packed with ProPak elements representing an efficiency of 15 theoretical plates, is fed at its middle with crude AA and at the top with MIBK, in an MIBK/water contained in the crude AA weight ratio of 3/1. A solution of stabilizers in MIBK is injected continuously at the top of the column, containing the stabilizers hydroquinone, phenothiazine and butyl dibutyldithiocarbamate (respectively: 35 ppm, 70 ppm and 35 ppm relative to the acrylic acid contained in the feed stream). The azeotropic mixture distills at an overhead temperature of 45° C. under a pressure of $1.2 \times 10^4$ Pa.

The dehydrated acrylic acid recovered at the bottom of the column contains no more than 0.4% water.

It is sent, stage (5), as feed for a topping column, which makes it possible to remove at the top, the light compounds, essentially acetic acid. This column, packed with ProPak elements (20 theoretical plates) is fed at its middle with the dehydrated AA stream, and at the top a stream rich in acetic acid is distilled under a pressure of $1.3 \times 10^4$ Pa, at an overhead temperature of 77° C., with a reflux ratio of 7/1. Introduced at the top of the distillation column is a solution of stabilizers in technical acrylic acid containing the stabilizers hydroquinone and butyl dibutyldithiocarbamate (400 ppm relative to the acrylic acid contained in the feed stream). The recovery yield of acrylic acid in this stage is 97%.

The topped acrylic acid recovered at the bottom of this column has a content of acetic acid of 0.07%. It is sent, stage (6) as feed for a tailing column packed with 17 perforated plates containing downcomers, which makes it possible to remove the heavy compounds as bottoms. This column operates under a pressure of $6.7 \times 10^3$ Pa, with an overhead temperature of 73° C., and with a reflux ratio of 0.5/1. Introduced at the upper plate of the distillation column is a solution of stabilizers in technical acrylic acid containing the stabilizers phenothiazine and butyl dibutyldithiocarbamate (400 ppm relative to the acrylic acid contained in the feed stream), and the condensed distillate stream has a solution of hydroquinone in pure AA (200 ppm relative to the distilled acrylic acid) added to it. The acrylic acid obtained at the top of the column constitutes the technical acrylic acid (TAA).

The analyses of the technical grade acrylic acid show that the product contains 0.07% acetic acid, 0.66% propionic acid, 0.11% maleic anhydride, 0.11% water, 0.023% 2-butenoic acid, 0.01% furfural, 0.02% benzaldehyde, 0.01% protoanemonin and 0.02% acrolein.

The recovery yield of the acrylic acid in this stage is 95.5%.

EXAMPLE 4

Purification of the Ex-Glycerol Technical AA by Crystallization

The stream of acrylic acid of technical grade obtained in example 3 is subjected to a series of steps of purification and concentration by fractional crystallization, as described in the present patent application. The arrangement used is a falling stream crystallizer composed of a vertical stainless steel tube filled with heat-exchange fluid (ethylene glycol/water mixture) circulating in a closed circuit, via a pump, through an external heat exchanger which can be programmed as a temperature gradient (Lauda cryostatic bath). This tube is fed at the top in the form of a liquid film which flows uniformly over its external wall. The liquid composed of the mixture to be crystallized, recovered in a receiving tank at the bottom, recirculates as a loop in a lagged circuit in order to again feed the tube at the top, via a pump.

The stream of technical acrylic acid is subjected to a series of several successive purification steps, each step comprising the following stages:
  crystallization: the heat-exchange fluid is rapidly cooled, so as to lower the temperature of the falling film of acrylic acid down to the temperature of crystallization of the acrylic acid in the mixture, determined beforehand from a sample of the mixture to be purified, and then a negative temperature gradient, of 0.1 to 0.5° C./min, is imposed on the heat-exchange fluid. When the volume of crystallized acrylic acid, measured by difference by evaluating the level of liquid in the collecting container at the bottom of the crystallizer, reaches 70% of the starting mixture, the recirculation of the falling film of mixture to be purified is halted and the tube is drained. The liquid mixture of the mother liquors thus obtained is separated and stored in a receiver.
  sweating: the heat-exchange fluid is reheated, so as to bring about the melting of a portion (5%) of the layer of crystallized acrylic acid at the surface of the tube. The mother liquors from this sweating stage are collected and stored in the same receiver as the mother liquors from the preceding stage.
  melting: the heat-exchange fluid is rapidly reheated up to a temperature of 30° C., until the crystallized layer has completely melted. The purified liquid stream is placed in a different receiver.

The product purified by melting in the final stage of the first purification step is conveyed to the second purification step, where it will be subjected to a new series of the 3 purification stages under the same operating conditions. The mother liquors from the second purification step are subsequently mixed with a fresh charge of the feed stream of technical AA in step 1. This process is thus repeated until the desired grade is obtained in the molten purified product.

In order to limit the losses of acrylic acid which are concentrated in the mother liquors from the first purification step, a series of successive concentration steps, exhibiting the same stages as the purification steps, is carried out in which the crystallisate from the "n−1" step is conveyed as feed of the "n" step and the mother liquors from this "n−1" step are conveyed as feed of the "n−2" step. These steps are carried out under the same operating conditions as the purification steps, except for the volume of crystallized acrylic acid targeted, before passing from the crystallization stage to the sweating stage, which is 60% of the product fed.

The final crystallization step is carried out in static mode. The stream to be purified is placed in a container made of stainless steel with a jacket through which circulates a cooled fluid maintained at the crystallization temperature of the medium, determined beforehand by a measurement of crystallization temperature. A vertical tube made of stainless steel filled with heat-exchange fluid (ethylene glycol/water mixture) circulating in a closed circuit, via a pump, through an external heat exchanger which can be programmed as a temperature gradient is immersed in this container.

In a first stage, the temperature of the heat-exchange fluid in the tube is rapidly lowered to the crystallization temperature of the medium and then a negative temperature gradient of 0.1 to 0.5° C./min is imposed. When the crystallized volume reaches approximately 50% of the starting material, the mother liquors are removed, a sweating stage is then carried out and, finally, the melting stage is carried out, as in the upper crystallization steps in dynamic mode.

Applied to the technical acrylic acid obtained from glycerol on completion of the purification stages of example 3, a sequence of 4 purification steps and 3 concentration steps, including a crystallization step in static mode, made it possible to obtain acrylic acid of "glacial" grade comprising 50 ppm of acetic acid, 410 ppm of propionic acid, less than 1 ppm of maleic anhydride, less than 80 ppm of water, less than 1 ppm of 2-butenoic acid, less than 1 ppm of furfural, less than 1 ppm of benzaldehyde, less than 1 ppm of protoanemonine and less than 1 ppm of acrolein.

The concentration of acrylic acid in the residual mother liquors from the final concentration step is 82%.

The AA recovery yield in this purification stage is 96.5%. Furthermore, the overall recovery yield of AA from the stream obtained after the azeotropic drying stage (4) is 92%.

With an additional concentration step in dynamic mode, i.e. 4 purification steps and 4 concentration steps, one of which in static mode, the AA concentration in the final mother liquors is 54.3% and the overall purification yield is 99.3%. The residue has the following composition by weight: AA: 54.3%; water: 7.3%; maleic anhydride: 8.9%; protoanemonin: 1%; benzaldehyde: 2%; acetic acid: 4.3%; propionic acid: 16.7%; acrolein: 1.6%; furfural: 0.8%; 2-butenoic acid: 2%.

EXAMPLE 5

Purification of the Ex-Glycerol Topped AA by Crystallization

The same treatment series with a static crystallization step are applied to the stream obtained at the bottom of the topping column (stage 5) from example 3.

A sequence of 4 purification steps and 3 concentration steps, including a static crystallization step, made it possible to obtain acrylic acid of "glacial" grade comprising less than 50 ppm of acetic acid, 500 ppm of propionic acid, less than 1 ppm of maleic anhydride, less than 100 ppm of water, less than 1 ppm of 2-butenoic acid, less than 1 ppm of furfural, less than 1 ppm of benzaldehyde, less than 1 ppm of protoanemonin and less than 1 ppm of acrolein.

The concentration of acrylic acid in the residual mother liquors from the final concentration step is 67%.

The AA recovery yield in this purification stage is 97%. Furthermore, the overall recovery yield of AA from the stream obtained after the azeotropic drying stage (4) is 94%.

EXAMPLE 6

Purification of the Ex-Glycerol Dried AA by Crystallization

The same treatment series with a static crystallization step are applied to the stream obtained at the bottom of the drying column (stage 4) from example 3.

A sequence of 4 purification steps and 2 concentration steps, including a static crystallization step, made it possible to obtain acrylic acid of "glacial" grade containing 1200 ppm of acetic acid, 450 ppm of propionic acid, less than 1 ppm of maleic anhydride, less than 100 ppm of water, less than 1 ppm of 2-butenoic acid, less than 1 ppm of furfural, less than 1 ppm of benzaldehyde, less than 1 ppm of protoanemonin and less than 1 ppm of acrolein.

The concentration of acrylic acid in the residual mother liquors from the final concentration step is 62%.

The overall recovery yield of AA from the stream obtained after the azeotropic drying stage (4) is 92%.

EXAMPLE 7 (COMPARATIVE)

Purification of the Ex-Glycerol Technical AA by Distillation

Added to the technical grade acrylic acid resulting from example 3 are phenothiazine (0.2%) and hydrazine hydrate in a molar ratio of 7/1 relative to the sum of the aldehydes (furfural, benzaldehyde, acrolein) and maleic anhydride present and the stream is distilled in a column having 17 perforated plates containing downcomers, under a pressure of $6.7 \times 10^3$ Pa, with an overhead temperature of 70° C. and a reflux ratio of 0.5/1.

Added to the condensed distillate stream is a solution of hydroquinone methyl ether (HQME) in glacial AA (200 ppm relative to the distilled acrylic acid).

The analyses of the acrylic acid obtained show that the product contains 0.07% acetic acid, 0.7% propionic acid, 3 ppm of maleic anhydride, 0.7% water, 75 ppm of 2-butenoic acid, less than 1 ppm of furfural, less than 1 ppm of benzaldehyde, 38 ppm of protoanemonin, and 2 ppm of acrolein. The recovery ratio of acrylic acid of this stage is 93%.

Furthermore, at the end of this last purification stage for obtaining the glacial AA grade, the recovery ratio of AA from the stream of the bottom of the azeotropic drying column from example 3 (stage (4)) is only 86%.

The acrylic acid produced according to the invention is a bioresourced acid manufactured from nonfossil natural starting materials.

The use of nonfossil carbon-based starting materials of natural origin can be detected by virtue of the carbon atoms participating in the composition of the final product. This is because, unlike fossil substances, substances composed of renewable starting materials comprise the radioactive isotope $^{14}C$. All carbon samples drawn from living organisms (animals or plants) are in fact a mixture of 3 isotopes: $^{12}C$ (representing ~98.892%), $^{13}C$ (~1.108%) and $^{14}C$ (traces: $1.2 \times 10^{-10}$%). The $^{14}C/^{12}C$ ratio of living tissues is identical to that of the $CO_2$ of the atmosphere.

The invariableness of the $^{14}C/^{12}C$ ratio in a living organism is related to its metabolism, with continual exchange with the atmosphere.

The disintegration constant of $^{14}C$ is such that the $^{14}C$ content is virtually constant from the harvesting of the plant starting materials up to the manufacture of the final product. The bioresourced acrylic acid obtained by the process of the invention has a content by weight of $^{14}C$ such that the $^{14}C/^{12}C$ ratio is greater than $0.8 \times 10^{-12}$ and preferably greater than $1 \times 10^{-12}$.

The measurement of the $^{14}C$ content of substances is clearly described in the standards ASTM D6866 (in particular D6866-06) and in the standards ASTM D7026 (in particular 7026-04).

The invention claimed is:

1. A process for the manufacture of bioresourced acrylic acid from glycerol, comprising the following stages:
    gas-phase catalytic dehydration of glycerol to give acrolein, (1)
    partial condensation by cooling and extraction of water and heavy impurities present in the reaction medium of (1), (1')
    gas-phase catalytic oxidation of a gas stream from (1') comprising water and acrolein in a molar ratio water/acrolein of 1.5/1 to 7/1 to give acrylic acid, (2)
    extraction of the acrylic acid present in the effluent stream from the oxidation by water absorption with cooling, (3)
    drying of a solution of the acrylic acid by distillation in the presence of a solvent that is immiscible with water, (4)
    distillation of a solution thus obtained in order to remove light compounds, (5)
    distillation of a heavy fraction resulting from (5) in order to remove heavy compounds, (6) a final extraction of the bioresourced acrylic acid by fractional crystallization applied to one of the following effluent streams: a heavy fraction from (4), the heavy fraction from (5) or a light fraction from (6).

2. The process as claimed in claim 1, wherein a liquid fraction resulting from (3) is subjected to a separation (3') from the residual acrolein by distillation or stripping with a gas.

3. The process as claimed in claim 1, wherein a heavy fraction from (4) is subjected to the final extraction of bioresourced acrylic acid by fractional crystallization.

4. The process as claimed in claim 1, wherein a heavy fraction from (5) is subjected to the final extraction of bioresourced acrylic acid by fractional crystallization.

5. The process as claimed in claim 1, wherein a light fraction from (6) is subjected to the final extraction of bioresourced acrylic acid by fractional crystallization.

6. The process as claimed in claim 1, wherein the final extraction of bioresourced acrylic acid is a fractional crystallization by a falling film fractional crystallization technique.

7. The process as claimed in claim 6, wherein the fractional crystallization comprises between 1 and 4 purifications and between 1 and 4 concentrations of impurities.

8. The process as claimed in claim 6, wherein the fractional crystallization is supplemented by concentration by static crystallization.

\* \* \* \* \*